United States Patent [19]

McVay et al.

[11] Patent Number: 5,543,565
[45] Date of Patent: Aug. 6, 1996

[54] METHOD FOR FORMING TWO TERMINAL CARBOXYLIC ACID GROUPS FROM AN OZONIDE

[75] Inventors: Kenneth R. McVay, Hamilton; Dennis G. Gaige, Fairfield; William S. Kain, Cincinnati, all of Ohio

[73] Assignee: Henkel Corporation, Plymouth Meeting, Pa.

[21] Appl. No.: 376,173

[22] Filed: Jan. 20, 1995

[51] Int. Cl.$^6$ .................................................. C07C 51/16
[52] U.S. Cl. ............................................................ 562/523
[58] Field of Search .............................................. 562/523

[56] References Cited

U.S. PATENT DOCUMENTS

| | | | |
|---|---|---|---|
| 2,601,223 | 6/1952 | Roedel | 562/523 |
| 2,813,113 | 11/1957 | Goebel et al. | 260/406 |
| 2,848,490 | 8/1958 | Niebling | 562/523 |
| 2,962,528 | 11/1960 | Skelly | 562/523 |
| 3,202,704 | 8/1965 | Perry | 562/523 |
| 3,223,730 | 12/1965 | Shulman | 562/523 |
| 3,280,183 | 10/1966 | Maggiolo | 562/523 |
| 3,284,492 | 11/1966 | Fremery | 562/523 |
| 3,441,604 | 4/1969 | Baylis | 562/523 |

FOREIGN PATENT DOCUMENTS

| | | |
|---|---|---|
| 0157315 | 12/1975 | Japan . |
| 4151906 | 11/1979 | Japan . |

*Primary Examiner*—Paul J. Killos
*Attorney, Agent, or Firm*—Ernest G. Szoke; Wayne C. Jaeschke; Daniel S. Ortiz

[57] ABSTRACT

The present invention is a process for the scission and oxidation of ozonide materials. The process comprises introducing an oxygen-containing gas stream into an agitated liquid body in the form of fine bubbles.

18 Claims, 2 Drawing Sheets

5,543,565

METHOD FOR FORMING TWO TERMINAL CARBOXYLIC ACID GROUPS FROM AN OZONIDE

FIELD OF THE INVENTION

The invention is a process for forming two terminal carboxylic acid groups from an ozonide of an unsaturated compound. Particularly, the process is directed to forming two terminal carboxylic acid groups from an ozonide of an unsaturated fatty body containing from about 8 to 30 carbon atoms. The process is particularly useful for preparing azelaic acid from the ozonide of oleic acid.

1. Background of the Invention

Terminal carboxylic acid groups can be formed in place of double bonds in organic chemical moieties by contact with strong oxidizing agents. However, the methods are not satisfactory since large amounts of unwanted byproducts are formed.

2. Related Art

U.S. Pat. No. 2,813,113, which is incorporated herein by reference, discloses a method for forming two terminal carboxylic acid groups in place of double bonds of unsaturated fatty bodies containing from 10 to 24 carbon atoms. The reference discloses that first an ozonide is formed by contacting the unsaturated fatty body at a temperature of less than about 45° C. with a mixture of oxygen and ozone.

The ozonide formed in the first step is then contacted with oxygen at a temperature above the scission temperature of the ozonide to cleave the ozonide and oxidize the scission products to the carboxylic acid groups. U.S. Pat. No. 2,813,118 teaches:

"In general the splitting and oxidizing of the ozonides requires from 4 to 8 hours depending upon the efficiency of the equipment in effecting intimate contact between the oxygen and the ozonides. While most ozonides are supposed to decompose promptly when their temperature is elevated above the temperature of scission and while aldehydes are supposed to be oxidized relatively easily, still the reaction seems to proceed relatively slowly and the desired high yields of azelaic acid are obtained only by continuing the process over a substantial period of time until as much oxygen as possible has been added to the mixed oxidation products. While the gaseous oxygen seems to react readily with the aldehydes and generate substantial heat during the initial period of contact, still the reaction goes to completion slowly and there is considerable indication that the ozonides do not split automatically and immediately upon being brought to the temperature of scission."

It would therefore be useful to provide a process which increased the scission rate and the rate at which the aldehydes reacted with the oxygen.

BRIEF DESCRIPTION OF THE INVENTION

According to the present invention, the rate of scission of the ozonide and oxidation of the aldehydes are substantially increased by introducing the oxygen into a liquid body comprising the ozonide and/or the aldehyde in the form of fine bubbles with a diameter of less than about 100μ. The oxygen-containing gas is introduced into the liquid body comprising the ozonide or its scission products in the form of fine bubbles. The fine bubbles can be formed by mechanical means, can be formed by passing the oxygen through a means which has openings sufficiently small to provide bubbles with the required size or by a dissolved gas technique. The liquid body can optionally contain a catalyst to further improve the rate of reaction. The scission or oxidation is carried out at a temperature from about 50° C., to about 150° C., preferably from about 90° C. to about 130° C.

DETAILED DESCRIPTION OF THE INVENTION

The process for preparing the ozonide by reaction of an ozone-containing gas with a compound having double bonds and particularly a fatty body is well known and is disclosed in U.S. Pat. No. 2,813,113. The process disclosed is shown in block diagrams in FIG. 1. The patent is directed to the formation of ozonides with unsaturated fatty acid and fatty acid derivatives such as fatty acid esters, fatty acid nitriles, fatty acid amides, soaps and the like. The process is also useful for reacting olefin compounds to form two monocarboxylic acids.

Figure 1:
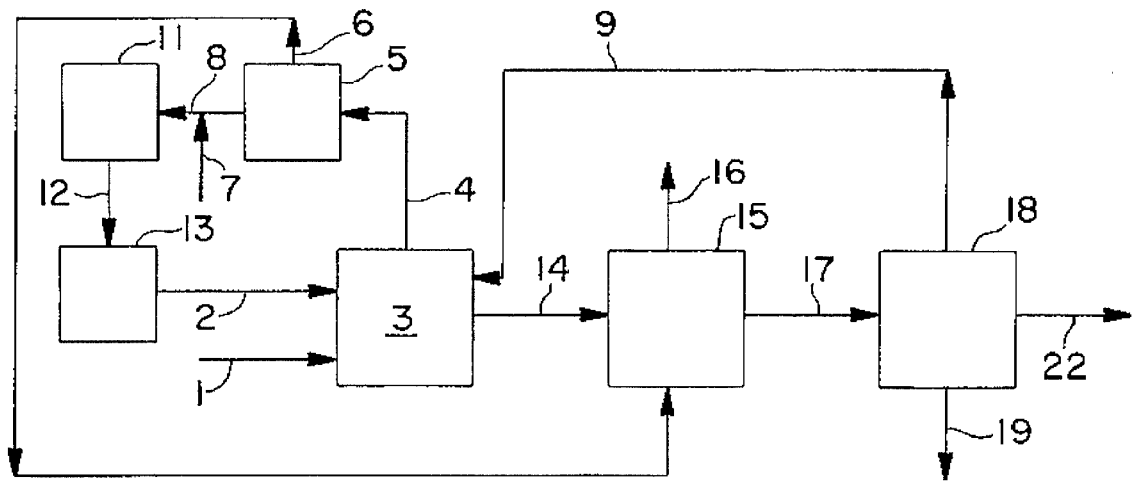
FIG. 1 is a block diagram of the process disclosed in U.S. Pat. No. 2,813.113.

As shown in FIG. 1, an unsaturated compound such as oleic acid is introduced into the ozone absorber 3 through line 1. An ozone-containing gas enters the ozone absorber 3 through line 2. The rate of feed of the oleic acid to the ozone absorber and the rate of introduction of the ozone-containing gas is adjusted so that the unsaturated compound is substantially fully reacted with the ozone. In the case of oleic acid, the oleic acid increases in weight by about at least 17% due to the reaction of the double bond with ozone.

The formation of the ozonides and oxidation to form two carboxylic acid groups is generally applicable to compounds containing olefinic double bonds. Particularly the process is useful for forming carboxyl groups in compounds containing from about 8 to about 30 carbon atoms in the group with the double bond. Fatty bodies such as carboxylic acids, their nitriles, amides, esters and the like or alkene compounds can be used as feed to the process. Commercially at the present time the process is particularly useful for preparing azelaic acid from oleic acid.

The oxygen leaves the ozone absorber through line 4 after its ozone content has been substantially reacted. The oxygen stream in line 4 then passes to gas-conditioning zone 5, where particulate matter is removed, the gas compressed and cooled and passed through line 8 to gas drier 11. A stream of oxygen passes out of the conditioning zone 5 through line 6. The oxygen which leaves the system through line 6 maintains the level of inert gas in the ozone generator and ozone absorber at a low level. The oxygen which is removed from the recycle system is used in scission of the ozonide and oxidation of the aldehydes formed. An amount of high purity oxygen enters line 8 through line 7 to maintain the inert gasses in the circulating stream at a low level. The recycled oxygen from zone 5 and the additional oxygen added through line 7 pass to gas drier 11 where the oxygen is dried. As one skilled in the art would understand, moisture in an oxygen containing gas stream substantially reduces the efficiency of an ozone generator. The dried oxygen-containing gas stream passes to the ozone generator 13 wherein a portion of the oxygen in the gas stream is converted to ozone and the oxygen gas stream containing the ozone passes through line 2 to ozone absorber 3.

In ozone absorber 3, the oleic acid reacts with the ozone to form an ozonide. The residence time in the ozone absorber is sufficient for the ozone to be removed from the oxygen stream and the oleic acid to absorb substantially the theoretical amount of ozone which is about 17% by weight of the oleic acid. However, generally larger amounts of ozone are absorbed due to the fact that the oleic acid is not 100% pure and other unsaturated materials can be present. Generally, the amount of ozone absorbed in ozone absorption zone 3 is from about 17 to about 19% by weight of the unsaturated oleic acid feed. The oxygen stream depleted in ozone leaves the ozone absorber 3 through line 4 and is recycled through the gas conditioning zone, drier and ozone generator and returned to the ozone absorber.

The product comprising the ozonide leaves the ozone absorber through line 14 and passes to an ozonide scission and oxidation zone 15. In the scission and oxidation zone 15, the ozonide is split and the resulting aldehydes are oxidized to form carboxylic acid groups. The oxygen used for the scission and oxidation enters the scission and oxidation zone 15 through line 6. The oxygen is preferably the gas which must be bled from the circulating ozonation system to maintain the concentration of inert gas at a low level. The inert gas and unreacted oxygen leave the scission and oxidation zone through line 16 and is discarded.

Scission and oxidation zone 15 can comprise one reactor or several reactors to provide a sufficient amount of contact and reaction time to cleave substantially all of the ozonides to form carboxyl groups and aldehyde groups and for oxidation of the aldehyde groups. The number of reactors is a design consideration and can range from 1 to about 8 or more, depending upon the residence time required, and the arrangements for cooling or heating the reactors.

In the ozonide scission and oxidation zone 15, the product from the ozone absorber is heated to a temperature above the scission temperature which is generally above 50° C. and preferably in the range of about 90° to 150° C. And more preferably from about 90° C. to about 130° C. If more than one reactor is utilized in the scission and oxidation zone 15, the first reactors generate a substantial amount of heat due to the scission and oxidation and generally require cooling to maintain the temperature in the desired range. However, in the subsequent reaction zones, the amount of heat generated is reduced and can require additional added heat to maintain the temperature in the range of 90° to about 150° C.

The number of reactors in the scission and oxidation zone is dependent upon design considerations and the apparatus available to remove the heat of the reaction at the beginning, to provide a sufficient residence time for the scission of ozonide and oxidation of the residues to provide a low level of unreacted aldehyde and to provide sufficient length of contact time to react a major portion of the oxygen in the oxygen containing gas stream entering the scission and oxidation zone.

The product from the scission and oxidation zone passes through line 7 to product recovery zone 18. In product recovery zone 18, the desired products are separated from the reaction mixture containing low boiling materials and high boiling tars which may have been formed during the process. The product leaves the process recovery zone through line 22 and the waste products leave the product recovery zone 18 through line 19.

In the process, upon absorption of ozone, the viscosity of the unsaturated compound can increase. If the ozonides have a substantially greater viscosity than the unsaturated compounds from which they are derived, it may become difficult to agitate the material to contact the ozone-containing oxygen stream and to ensure scission and reaction of the scission products with oxygen. To reduce the viscosity of the material in the ozone absorber and the scission and oxidation reactors, a solvent can be introduced into the ozone absorber to maintain the reaction mixture at a reduced viscosity. The solvent can be known materials which do not readily react with ozone and which are solvents for the ozonides or the reaction products, or can be a portion of the reaction product. As shown in FIG. 1, a diluent stream passes from the product recovery zone 18 through line 9 to the ozone absorber 3 to maintain the viscosity of the reaction mixture at a suitable level. The viscosity control material can be solvents such as benzene toluene or materials such as low molecular weight alcohols and the like. However, it is preferred that a portion of the product be recycled to the ozone absorber to maintain the viscosity at the required level. Recycle of a portion of the product is the preferred method for controlling the viscosity, since the process does not require an additional solvent recovery and separation system. The details of the process are more fully set out in U.S. Pat. No. 2,813,113, the contents of which are incorporated herein by reference.

Figure 2:
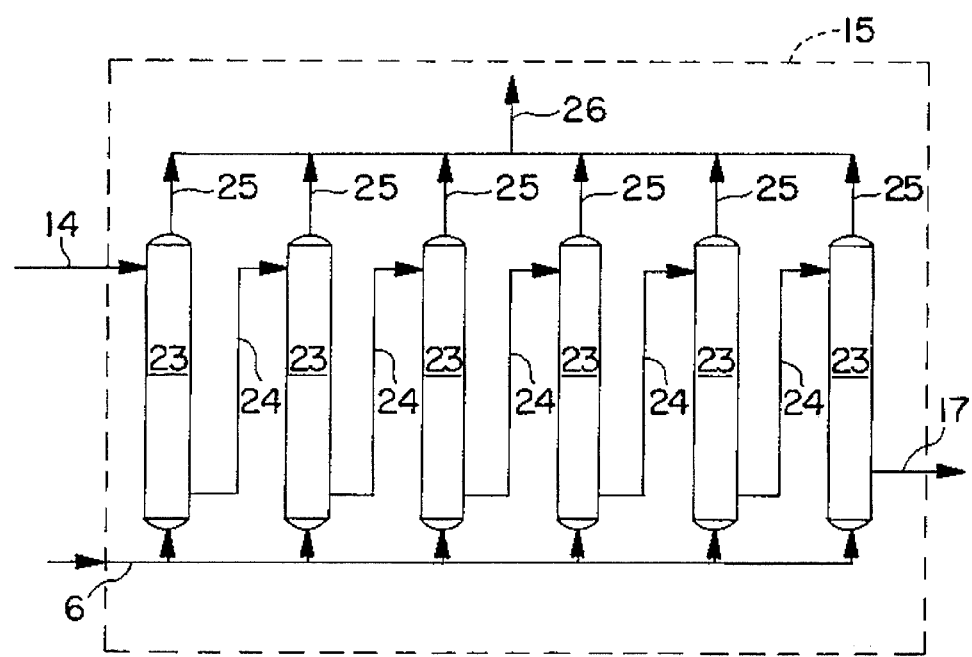
FIG. 2 is a schematic representation of the reactor configuration for scission of the ozonides and oxidation of the aldehydes.

FIG. 2 illustrates an ozonide scission and oxidation zone 15 which is within the dotted line. The ozonide scission and oxidation zone as shown comprises 6 reactors 23 in which the ozonide product from the ozone absorber enters the first reactor 23 through line 14 then cascades from reactor to reactor through line 24 and passes to the product recovery zone through line 17. The number of reactors (six) shown in FIG. 2 is an arbitrary number and is solely dependent upon design considerations in regard to heat removal or heat addition, residence time of the product in the scission and oxidation zone and contact time between the oxygen containing gas and the reaction mixture. Although six reactors are shown, two to about eight or ten reactors are generally suitable for carrying out the scission and oxidation of the ozonide reaction product from the ozone absorber.

In the scission and oxidation zone 15 shown in FIG. 2, which comprises the six reactors, the first three reactors 23 in the system would generate heat and require an amount of cooling. Clearly, as the amount of ozonide and aldehydes in the mixture decreases by scission and oxidation, the amount to be reacted is reduced and the amount of material reacted in a time period decreases.

As shown in FIG. 2, the oxygen containing gas stream which is removed from the circulating gas stream in the ozone absorption, gas conditioning and ozone generating zone is passed to the scission and oxidation zone through line 6. The flow of oxygen containing gas is controlled to each reactor to ensure that a substantial portion of the oxygen in the gas stream is reacted so that only a small amount of oxygen leaves the system through lines 25 and 26 to be discarded. The gas bled from the ozone process is used in the scission and oxidation zone but it would be understood that other sources of oxygen are suitable.

As the concentration of materials to be cleaved and oxidized decreases, the temperature of the material in the reactors is generally maintained by heating the contents of the reactor to the required temperature range. It is known that the rate of reaction between the ozonide and ozonide reaction products with oxygen can be increased by introducing a catalyst into the mixture. Oxidation catalysts such as chromium, manganese, iron, cobalt and the like have been found to be useful to increase the rate of reaction between the oxygen-containing gas and the reaction mixture. In particular, catalysts are known to increase the rate of reaction between the aldehydes and the oxygen-containing gas. The catalyst can be introduced into any of the reactors in the system. However, in the initial reactors where the, amount of scission and oxidation of the aldehydes is substantial, the addition of catalysts to the reaction mixture may make it more difficult to control the reaction temperature in the required range. However, in reactors in which heat is introduced to maintain the reaction mixture in the required temperature range, catalysts can be introduced into the reaction mixture to substantially increase the reaction rate.

Manganese is an excellent catalyst for the process. The manganese can be introduced into the process in the form of a soluble material or in the form of a solid or supported catalyst. Preferred catalysts are reaction products of manganese with aliphatic carboxylic acids or manganese supported on materials such as activated carbon, alumina, zeolites (see U.S. Ser. No. 08/195,944), titania and the like. The soluble catalysts are separated from the reaction products in the tar-like waste streams. The insoluble catalysts can be separated from the reaction mixture by liquid solid separation means such as a filter, liquid cyclone, centrifugal separator and the like. The soluble catalysts are generally discarded with the tars and waste products from the process while the insoluble catalysts can be recycled to the process. The addition of the catalysts to the reacting mixture substantially increases the rate at which the scission of the ozonide and oxidation of the aldehydes occurs.

U.S. Pat. No. 2,823,113 discloses at column 5, lines 1–6 that "the gaseous oxygen seems to react readily with the aldehydes and generate substantial heat during the initial period of contact, still the reaction goes to completion slowly and there is considerable indication that the ozonides do not split automatically and immediately upon being brought to the temperature of scission".

In the face of the teachings of U.S. Pat. No. 2,813, 113, Applicants have discovered that if the oxygen is introduced into an agitated body of liquid reaction mixture, in the form of fine bubbles, the rate of reaction can be substantially increased. Applicants have discovered that when the oxygen-containing gas is introduced into the reaction mixture in a manner such that the bubble size is in the range of less than 100 microns and preferably less than about 25 microns and more preferably less than 10 microns, the rate of reaction between the carbonyl groups in the reaction mixture and the oxygen-containing gas is substantially increased. The increased rate of reaction can reduce the amount of catalyst introduced into the system, can reduce the size of the reactors, since the residence time can be reduced or increase the throughput of the reactor system.

It is critical to the invention that the oxygen-containing gas be introduced into the reactors in the form of fine bubbles. In addition, the reactors must be agitated to adequately distribute the fine bubbles throughout the reaction mixture. Prior to the present invention, oxygen-containing gas was sparged into the bottom of the reactor through a fine open tube and the reaction mixture vigorously agitated.. Applicants have discovered that the reaction rate can be increased by a factor of about 4 to about 8 by introducing the oxygen-containing gas into the mixture in the form of fine bubbles.

The fine bubbles can be generated by any means known in the art. The fine bubbles can be generated by mechanical means such as a flotation machine by passing the reaction mixture and the oxygen through a high shear zone to form the fine bubbles. This technique is generally used in froth flotation cells and is well known in the art. The fine bubbles can also be generated by the dissolved gas technique. That is, all or a portion of the liquid phase entering a reaction zone is contacted with the oxygen-containing gas at an elevated pressure. The oxygen-containing gas dissolves in the liquid phase and when the pressure is removed by passing the liquid into the reactor, the dissolved gases leave the liquid phase in the form of fine bubbles. The gas can be dissolved in all of the liquid phase entering the reactor or can be dissolved in only a portion of the liquid phase. Generally, it may be necessary to cool the reaction mixture to a temperature in which the oxygen is soluble in the liquid phase at the elevated pressure. This technique generates extremely fine bubbles which appear to be a cloudiness in the liquid or somewhat like smoke. The oxygen can be introduced into the reaction mixture through a porous membrane, a porous metal such as sintered metal, fritted glass or porous ceramics. The method of introducing the oxygen-containing gas into the agitated body of liquid reaction mixture in the form of fine bubbles would be well known to one skilled in the art.

The oxygen-containing gas in the form of fine bubbles can be introduced into the reaction mixture containing a catalyst as discussed above or the reaction mixture can be catalyst-free. In any case, the introduction of the oxygen-containing gas in the form of fine bubbles into an agitated body of the liquid reaction mixture substantially increases the rate of reaction. Contrary to the teachings of U.S. Pat. No. 2,813, 113, the reaction can be made to go to completion rapidly when the oxygen-containing gas is introduced into the reaction mixture in the form of fine bubbles.

The pressure in the scission and oxidation zone is not critical and generally ranges from above about atmospheric pressure to about 100 psi. Higher pressures can be used but generally the increased cost of the pressure equipment makes use of higher pressures uneconomical.

EXAMPLE

The effect of introducing the oxygen-containing gas into the reaction mixture in the form of fine bubbles was determined in the following manner. A sample of a liquid reaction mixture of an oleic acid ozonide containing pelargonic acid diluent to reduce the viscosity, which had been partially reacted with oxygen, was prepared and utilized as the feed stock for this experiment. The partially oxidized reaction mixture was stored in a refrigerator under a nitrogen blanket until the material was utilized. The partially oxidized feedstock was placed in a 500 ml four neck round bottom flask fitted with adapters for thermometer, shaft for the stirrer, gas inlet, gas outlet and sampling means. A water condenser and a dry ice/acetone cooled vapor trap were connected to the gas outlet port. The temperature of the reaction vessel was controlled by a computer-controlled hot plate with a probe. The temperature was controlled within ±5° C. The flask was equipped with a CAFRAMO Digital 2000 stirrer motor with a 2" long mixing blade. The agitator speed was controlled at 100 rpm.

250 g of the partially oxidized feedstock was introduced into the flask. 6.4 g of manganese acetate catalyst was added to the feedstock to provide a manganese concentration of 1600 ppm. After the catalyst had been introduced into the partially oxidized mixture, the stirrer was turned on and nitrogen was introduced into the mixture and the mixture heated to 120° C. When the mixture had reached the reaction temperature of 120° C., the nitrogen sparge was discontinued and oxygen was sparged into the mixture. Samples were taken periodically and the carbonyl values of the samples were determined by reacting the unreacted, residual carbonyl components with 2,4 dinitrophenylhydrazine and measuring the light absorption of the sample. In the first experiment, the oxygen was introduced into the reaction mixture through a tube with an opening of 1.3 mm. In a second experiment, the oxygen was introduced into the reaction mixture through a fritted glass disk 10 mm in diameter with a maximum pore diameter of 50 microns. The open tube with a diameter of 1.3 mm was positioned near the bottom of the flask. The fritted glass disk was positioned at the bottom of the flask. Oxygen was introduced into the system at the rate of 2 standard cubic feet per hour. After 5 hours, the oxygen flow was terminated and nitrogen was bubbled through the reaction mixture and the mixture was permitted to cool. Table 1 shows the results of the experiment.

TABLE 1

| Time of Sample (hours @ 120° C., 100 rpm) | Control Open Tube Oxygen Probe | Experimental Fritted Oxygen Probe |
| --- | --- | --- |
| 0 | 6410 | 6150 |
| 0.5 | 5720 | 3250 |
| 1.0 | 5340 | 1670 |
| 2.0 | 4370 | 550 |
| 3.0 | 3490 | 440 |
| 5.0 | 2270 | finished |

Figure 3:
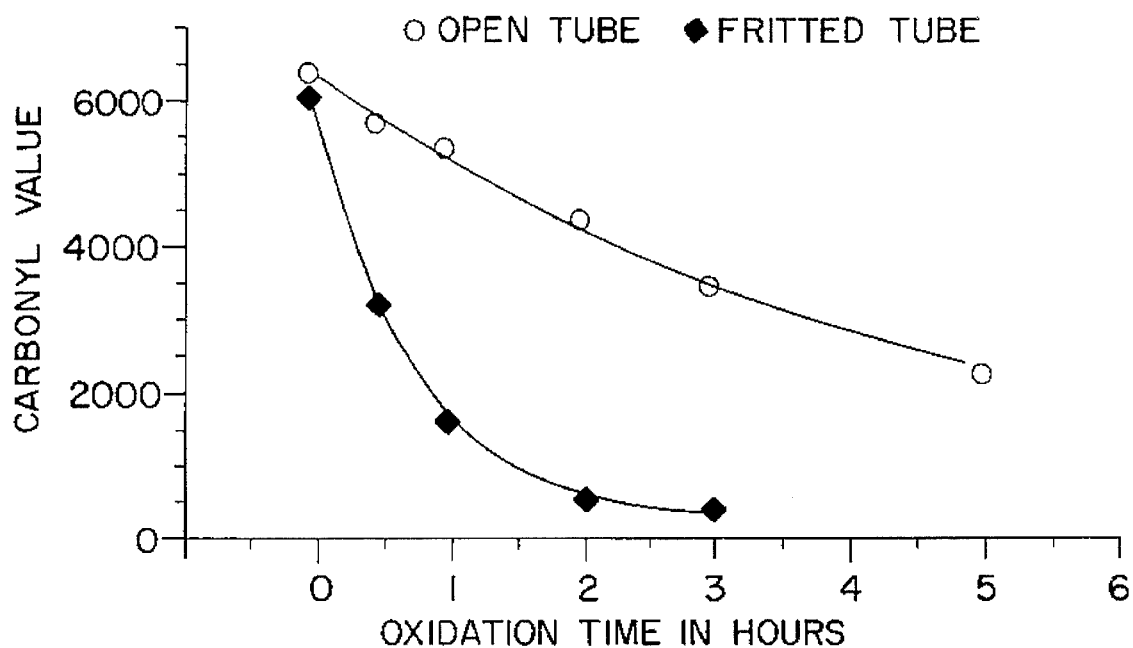
FIG. 3 is a plot of the data of Table 1.
Figure 4:
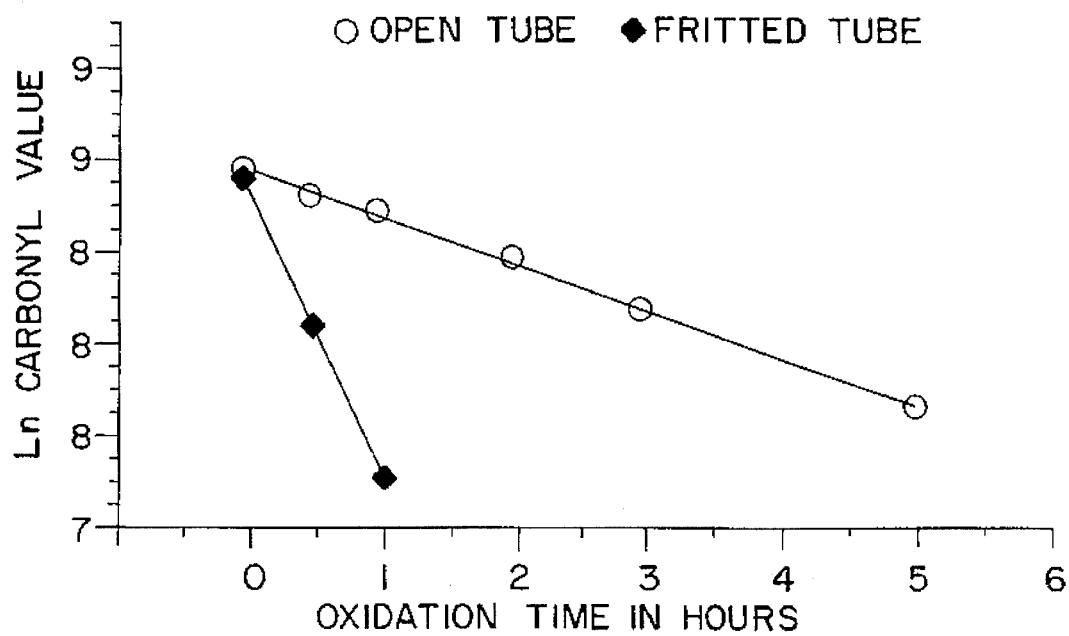
FIG. 4 is a ln plot of the data of Table 1.

FIG. 3 is a plot of the data of Table 1. FIG. 4 is a ln plot of the data from Table 1. The ln plot clearly shows that the rate constant for reaction in the reactor in which the oxygen was introduced into the mixture through the fritted disk was much higher than the rate constant for the reaction in which the oxygen was introduced into the action mixture through a 1.3 mm tube. The slope of the line (first order rate constant) associated with the fritted sparger can be seen to be greater than six times the slope of the line associated with the open tube sparger.

In view of the six-fold increase in the reaction rate constant, it is clear that the amount of catalyst used could be reduced, the residence time and therefore the size of the reactor can be reduced or the throughput of the apparatus increased.

It is necessary to reduce the carbonyl value of the reaction mixture to provide a material with a low and stable color value.

The invention is an advance in the art since prior to the discovery it was believed that the scission and oxidation reactions were slow and required long reaction times to go to substantial completion (low carbonyl values below about 500 ppm).

We claim:

1. In a process for the formation of two terminal carboxylic acid groups from a mixture comprising an ozonide containing from about 8 to about 30 carbon atoms in the chain containing the ozonide moiety by contacting the mixture comprising at least one of the ozonide or oxidizable ozonide scission products with oxygen at a temperature of from about 50° C. to about 150° C. with an oxygen-containing gas, the improvement which comprises: introducing the oxygen-containing gas into an agitated liquid mixture comprising at least one of the ozonide or the oxidizable ozonide scission products in the form of bubbles with a diameter of less than 100 microns.

2. The process of claim 1 wherein the temperature is from about 90° C. to about 130° C.

3. The process of claim 1 wherein the liquid mixture comprising the ozonide contains a viscosity reducing amount of a solvent.

4. The process of claim 1 wherein the liquid mixture comprising the ozonide further comprises an oxidation catalyst.

5. The process of claim 4 wherein the catalyst comprises a composition containing a metal selected from the group consisting of chromium, manganese, iron and cobalt.

6. The process of claim 4 wherein the oxidation catalyst is a soluble catalyst.

7. The process of claim 4 wherein the oxidation catalyst comprises a solid catalyst.

8. The process of claim 7 wherein the solid catalyst is a supported catalyst.

9. The process of claim 8 wherein the catalyst is a supported manganese catalyst.

10. The process of claim 6 wherein the catalyst is a soluble manganese catalyst.

11. The process of claim 3 wherein the liquid mixture comprising the ozonide further comprises an oxidation catalyst.

12. The process of claim 11 wherein the catalyst is a manganese catalyst.

13. The process of claim 12 wherein the manganese catalyst is a soluble catalyst.

14. The process of claim 12 wherein the manganese catalyst is a supported manganese catalyst.

15. The process of claim 1 wherein a carbonyl value of the mixture is reduced to less than about 500 ppm.

16. The process of claim 4 wherein a carbonyl value of the mixture is reduced to less than 500 ppm.

17. The process of claim 10 wherein a carbonyl value of the mixture is reduced to less than about 500 ppm.

18. The process of claim 14 wherein a carbonyl value of the mixture is reduced to less than about 500 ppm.

* * * * *